(12) United States Patent
Shifrin et al.

(10) Patent No.: US 9,355,208 B2
(45) Date of Patent: May 31, 2016

(54) DETECTING DEFECTS ON A WAFER

(71) Applicant: KLA-Tencor Corporation, Milpitas, CA (US)

(72) Inventors: Eugene Shifrin, Sunnyvale, CA (US); Ashok Kulkarni, San Jose, CA (US); Kris Bhaskar, San Jose, CA (US); Graham Michael Lynch, Singapore (SG); John Raymond Jordan, III, Mountain View, CA (US); Chwen-Jiann Fang, Palo Alto, CA (US)

(73) Assignee: KLA-Tencor Corp., Milpitas, CA (US)

( * ) Notice: Subject to any disclaimer, the term of this patent is extended or adjusted under 35 U.S.C. 154(b) by 0 days.

(21) Appl. No.: 14/321,565

(22) Filed: Jul. 1, 2014

(65) Prior Publication Data
US 2015/0012900 A1    Jan. 8, 2015

Related U.S. Application Data

(60) Provisional application No. 61/843,862, filed on Jul. 8, 2013.

(51) Int. Cl.
*G06F 17/50* (2006.01)
*G01N 21/95* (2006.01)
*H01L 21/66* (2006.01)

(52) U.S. Cl.
CPC ........ *G06F 17/5081* (2013.01); *G01N 21/9501* (2013.01); *H01L 22/12* (2013.01); *G06F 17/5045* (2013.01)

(58) Field of Classification Search
CPC ............... G06T 2207/30148; G06T 7/0006; G03F 1/84; G03F 7/7065; G03F 17/5045; G03F 17/5081; G01N 21/9501
USPC ...................... 716/112, 51, 52, 136
See application file for complete search history.

(56) References Cited

U.S. PATENT DOCUMENTS

| | | | |
|---|---|---|---|
| 7,334,212 B2 * | 2/2008 | Zach ................................ 716/53 |
| 7,345,753 B2 * | 3/2008 | Bhaskar et al. ............ 356/237.5 |
| 7,570,796 B2 * | 8/2009 | Zafar et al. .................... 382/144 |
| 7,676,077 B2 * | 3/2010 | Kulkarni et al. .............. 382/144 |
| 7,769,225 B2 * | 8/2010 | Kekare et al. ................. 382/145 |

(Continued)

FOREIGN PATENT DOCUMENTS

| | | |
|---|---|---|
| WO | 2010/093733 | 8/2010 |
| WO | 2013/040063 | 3/2013 |

OTHER PUBLICATIONS

International Search Report and Written Opinion for PCT/US2014/045601 mailed Oct. 14, 2014.

*Primary Examiner* — Helen Rossoshek
(74) *Attorney, Agent, or Firm* — Ann Marie Mewherter

(57) ABSTRACT

Systems and methods for detecting defects on a wafer are provided. One method includes determining locations of all instances of a weak geometry in a design for a wafer. The locations include random, aperiodic locations. The weak geometry includes one or more features that are more prone to defects than other features in the design. The method also includes scanning the wafer with a wafer inspection system to thereby generate output for the wafer with one or more detectors of the wafer inspection system. In addition, the method includes detecting defects in at least one instance of the weak geometry based on the output generated at two or more instances of the weak geometry in a single die on the wafer.

37 Claims, 4 Drawing Sheets

(56) References Cited

U.S. PATENT DOCUMENTS

| | | | |
|---|---|---|---|
| 7,796,804 B2* | 9/2010 | Bhaskar et al. | 382/145 |
| 8,041,103 B2* | 10/2011 | Kulkarni et al. | 382/144 |
| 8,102,408 B2* | 1/2012 | Verma et al. | 346/87 |
| 8,112,241 B2* | 2/2012 | Xiong | 702/117 |
| 8,139,843 B2* | 3/2012 | Kulkarni et al. | 382/144 |
| 8,194,968 B2* | 6/2012 | Park et al. | 382/145 |
| 8,213,704 B2* | 7/2012 | Peterson et al. | 382/145 |
| 8,559,001 B2* | 10/2013 | Chang et al. | 356/237.5 |
| 8,923,600 B2* | 12/2014 | Zafar et al. | 382/144 |
| 2007/0156379 A1* | 7/2007 | Kulkarni et al. | 703/14 |
| 2007/0230770 A1* | 10/2007 | Kulkarni et al. | 382/149 |
| 2007/0288219 A1* | 12/2007 | Zafar et al. | 703/14 |
| 2008/0072207 A1* | 3/2008 | Verma et al. | 716/21 |
| 2011/0170091 A1 | 7/2011 | Chang et al. | |
| 2011/0276935 A1* | 11/2011 | Fouquet et al. | 716/112 |
| 2011/0286656 A1* | 11/2011 | Kulkarni et al. | 382/144 |
| 2012/0050728 A1 | 3/2012 | Fayaz et al. | |
| 2012/0243773 A1 | 9/2012 | Kulkarni et al. | |
| 2013/0182101 A1* | 7/2013 | Yong et al. | 348/87 |
| 2014/0301629 A1* | 10/2014 | Ramachandran | 382/149 |

* cited by examiner

DETECTING DEFECTS ON A WAFER

BACKGROUND OF THE INVENTION

1. Field of the Invention

The present invention generally relates to systems and methods for detecting defects on a wafer.

2. Description of the Related Art

The following description and examples are not admitted to be prior art by virtue of their inclusion in this section.

Inspection processes are used at various steps during a semiconductor manufacturing process to detect defects on wafers to promote higher yield in the manufacturing process and thus higher profits. Inspection has always been an important part of fabricating semiconductor devices such as ICs. However, as the dimensions of semiconductor devices decrease, inspection becomes even more important to the successful manufacture of acceptable semiconductor devices because smaller defects can cause the devices to fail.

Some current inspection methods use standard images such as standard die images to detect defects on wafers. For example, a standard die image (also commonly referred to as a "golden die") be compared to a test die image acquired for a wafer being inspected and the results of the comparison may be input to a defect detection algorithm or method to determine if any defects are present in the test die. Such golden die images are commonly used for inspection of logic regions of dies since the logic regions of dies often do not include periodically repeating features that can be compared to one another for defect detection.

A disadvantage of using a standard die image for inspection is that, if the standard die image was acquired from a wafer other than the one being inspected, wafer-to-wafer noise can be relatively high and can interfere with defect detection or decrease the accuracy of defect detection. In addition, if the standard die image is acquired using the same wafer that is being inspected, die-to-die noise can also interfere with, or decrease the accuracy of defect detection. Furthermore, if the standard die image is generated using design data for the wafer, the standard die image may not adequately represent noise sources on the wafer thereby having the same disadvantages described above.

Accordingly, it would be advantageous to develop systems and methods for detecting defects on a wafer that do not have one or more of the disadvantages described above.

SUMMARY OF THE INVENTION

The following description of various embodiments is not to be construed in any way as limiting the subject matter of the appended claims.

One embodiment relates to a method for detecting defects on a wafer. The method includes determining locations of all instances of a weak geometry in a design for a wafer. The locations include random, aperiodic locations. The weak geometry includes one or more features that are more prone to defects than other features in the design. The method also includes scanning the wafer with a wafer inspection system to thereby generate output for the wafer with one or more detectors of the wafer inspection system. In addition, the method includes detecting defects in at least one instance of the weak geometry based on the output generated at two or more instances of the weak geometry in a single die on the wafer. The determining and detecting steps are performed with one or more computer systems.

Each of the steps of the method may be further performed as described herein. In addition, the method may include any other step(s) of any other method(s) described herein. Furthermore, the method may be performed by any of the systems described herein.

Another embodiment relates to a non-transitory computer-readable medium storing program instructions executable on a computer system for performing a computer-implemented method for detecting defects on a wafer. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

An additional embodiment relates to a system configured to detect defects on a water. The system includes an inspection subsystem configured to scan a water to thereby generate output for the wafer with one or more detectors of the inspection subsystem. The system also includes one or more computer subsystems configured for performing the determining and detecting steps of the method described above. The system may be further configured as described herein.

BRIEF DESCRIPTION OF THE DRAWINGS

Further advantages of the present invention will become apparent to those skilled in the art with the benefit of the following detailed description of the preferred embodiments and upon reference to the accompanying drawings in which.

Figure 1:
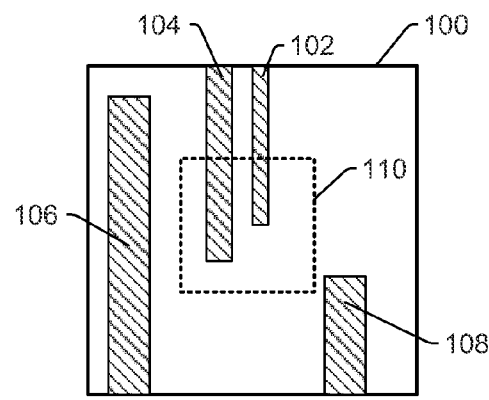
FIG. 1 is a schematic diagram illustrating a plan view of one embodiment of a pattern of interest (POI) in a design for a layer on a wafer and a micro care area (MCA) within the POI.

While the invention is susceptible to various modifications and alternative forms, specific embodiments thereof are shown by way of example in the drawings and are herein described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

The embodiments described herein relate to methods for detecting defects on a wafer. The methods may be used for detecting defects at certain "weak locations," also called "hot spots," in the design layout of a semiconductor chip at a particular layer of the chip. These are locations at which relatively small changes in the manufacturing process can lead to defects in patterning. An example is the lithography step where focus and exposure have to be relatively well controlled since relatively small changes in the focus or exposure can cause several instances of these structures on the die to fail. Failures can be "hard" failures, i.e. all or a substantial majority of the structures may fail, or "soft" failures, i.e. a relatively small fraction of the structures may fail.

Defect detection in most inspection systems is performed by comparing a given location in one die to the corresponding locations in its adjacent dies. In the case of periodic structures (such as arrays), one can compare a location in the die with a location some integral number of (array) cells away from the test location. The advantage of comparing cell-to-cell versus die-to-die is that there can be other noise sources between dies that reduce the sensitivity with which defects can be detected. For example, changes to the film thickness between one die and the next or slight changes in the focus plane of the inspector from die-to-die introduces noise that limits sensitivity. Noise in cell-to-cell comparisons is less because the distance between cells is much less than between dies.

It turns out that even in random logic areas, at the relatively small feature scales involved in today's designs, geometries repeat in thousands of locations within a die, though not at a fixed periodicity in x and y. These instances of identical geometries (within, say, a window of 100 nm×100 nm) may occur at numerous random locations within a die. If the design layout is available, given one example of a weak geometry, one can determine the locations of all instances of that geometry in a die. For example, the methods described herein include determining locations of all instances of a weak geometry in a design for a wafer. In this manner, the design may be utilized to get all hot spot locations on the wafer. The locations include random, aperiodic locations, and the weak geometry includes one or more features that are more prone to defects than other features in the design.

Given these locations, the detection algorithm can compare the corresponding image (pixels) at these locations in order to find the outliers, i.e., potential defects. For example, the methods described herein include scanning the wafer with a wafer inspection system to thereby generate output for the wafer with one or more detectors of the wafer inspection system and detecting defects in at least one instance of the weak geometry based on the output generated at two or more instances of the weak geometry in a single die on the wafer. This is the central concept behind the embodiments described herein. The determining and detecting steps are performed with one or more computer systems, which may be configured as described further herein.

The term "design" as used herein generally refers to the physical design (layout) of an IC and data derived from the physical design through complex simulation or simple geometric and Boolean operations. The design may be stored in a data structure such as a GDS file, any other standard machine-readable file, any other suitable file known in the art, and a design database. A GDSH file is one of a class of files used for the representation of design layout data. Other examples of such files include GL1 and OASIS files. The design used in the embodiments described herein may be stored in any of this entire class of files irrespective of data structure configuration, storage format, or storage mechanism.

Three possible methods are described below though other variations of these approaches can be developed. The three methods include a patch to standard reference patch (also referred to herein as a "golden patch") method; a patch to golden patch and standard reference defect (also referred to herein as a "golden defect") method; and an aggregate patch outlier detection method.

In the patch to golden patch method, we assume that the location in the design where the weak geometry (hot spot) exists is given. In one embodiment, the weak geometry is specified in a window at a point in design coordinate space, and a width d a height of the window are less than or equal to 100 nm. For example, the weak geometry is specified in the form of a window of a certain width and height located at a certain point in the design coordinate space. A typical window size might be 100 nm by 100 nm. We call this window a micro care area (MCA). Prior to inspection, the design database for this device/layer is searched for all instances of this MCA. In this manner, instances of the window in the design constitute at least some MCAs for inspection of the wafer. There may be thousands of such instances.

In an embodiment, the method includes creating a larger window around the window, and features in the larger window are used as a pattern of interest (POI) for inspection of the wafer. For example, for each such instance, we take a larger window around it (e.g., a 400 nm by 400 nm window). In this manner, given the locations of the hot spots (MCAs), bigger design clips around each location can be acquired, and this larger window is called the POI. In one such embodiment shown in FIG. 1, POI 100 is a window in a design for a layer of a wafer that includes features 102, 104, 106, and 108. The weak geometry in the POI may include the portions of features 102 and 104 in window 110. This window size may be equal or roughly equal to those described herein and the window may be used as an MCA for the inspection of that layer of the wafer.

The POI provides the local context around the MCA and is used to align the standard reference patch to the corresponding patch in the test die during inspection. For example, in one embodiment, the method includes determining design context for the weak geometry based on the features in the larger window. The design context may include any information related to the design such as criticality of the features in the weak geometry, electrical function of the features in the weak geometry, and the like. In another embodiment, detecting the defects includes aligning the features in the larger window to patch images in the output. Aligning the features in the larger window to patch images may be performed in any suitable manner (e.g., using a suitable pattern matching method and/or algorithm). The POI images can be created and saved in the wafer inspection recipe. In this manner, during an inspection run, we can find POIs with pixel accuracy and get MCA images.

In one embodiment, the method includes grouping all instances of the POI that are substantially the same into one bin and all other instances of POIs into one or more other bins. In this manner, all the POIs are divided into bins (groups) where each group includes identical patterns (geometries). There may be several such groups. For example, the design clips acquired around the locations of the hot spots (MCAs) on the wafer can be analyzed for similarity. Similar clips can be binned together, and POI locations and MCA-to-POI vectors can be calculated.

Figure 2:
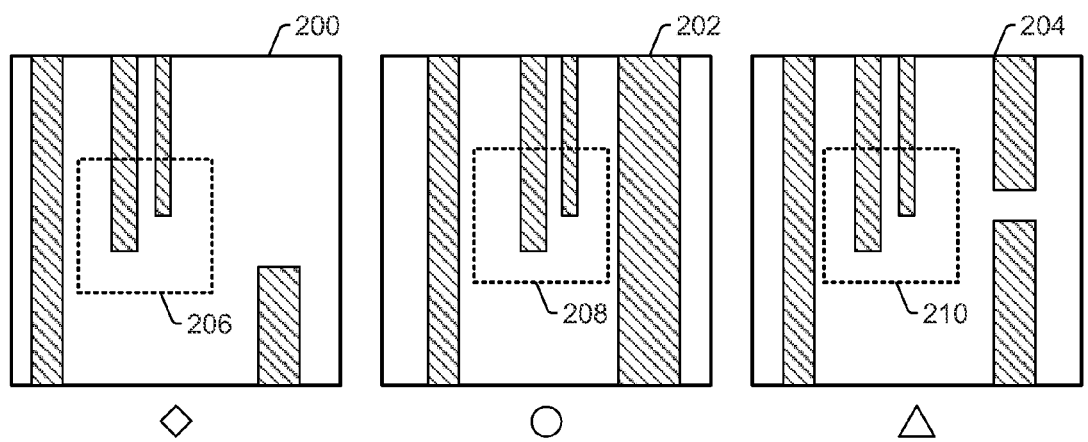
FIG. 2 is a schematic diagram illustrating a plan view of one embodiment of different POIs in a design for a layer on a wafer and locations of the different POIs in a die for the wafer.
Figure 2:
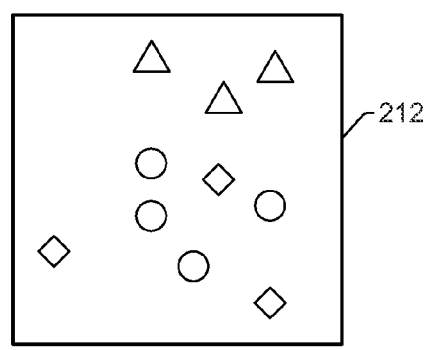

In one such example, as shown in FIG. 2, a die may include different POIs 200, 202, and 204 that include different or the same MCAs 206, 208, and 210, respectively. For example, surroundings of identical MCAs may be different in different parts of the die, so the POIs may be different for the same weak geometry. Any POIs 200 in the die may be binned into one group, e.g., Group 1, any POIs 202 in the die may be binned into another group, e.g., Group 2 that is different and separate from Group 1, and any POIs 204 in the die may be binned into a further group, e.g., Group 3 that is different and separate from both Groups 1 and 2.

Die 212 may include any number of each of the POIs. For example, die 212 may include 3 instances of POI 200 indicated in the die by the diamond shape under POI 200, 4 instances of POI 202 indicated in the die by the circle shape under POI 202, and 3 instances of POI 204 indicated in the die by the triangle shape under POI 204. Of course, the die may include any number of any of these POIs depending on the design for the layer of the wafer. In addition, as shown in die 212, the locations of the POIs within the die may be random and aperiodic in both x and y directions within the die. All POIs within a group would be identical to each other and different from POIs in another group. For instance, the POIs in Group 1 would all be identical to each other and different from the POIs in Groups 2 and 3, the POIs in Group 2 would all be identical to each other and different from the POIs in Groups 1 and 3, and the POIs in Group 3 would all be identical to each other and different from the POIs in Groups 1 and 2.

The standard reference patch may be a golden patch image created during the setup of the wafer inspection recipe. In one embodiment, the method includes generating a standard reference patch for the POI by acquiring an image of at least one instance of the POI with the wafer inspection system. For example, during the setup step for an inspection recipe for a device/layer, the inspection system may scan a die (or several dies) and construct a standard reference patch (golden patch) for each such group. This can be done in several ways. One could just use one instance of the image at a certain location (known from the design analysis step above). In addition, during the recipe setup, a user may provide a defect free area on the wafer.

Alternatively, in another embodiment, the method includes generating a standard reference patch for the POI from multiple image patches acquired by the wafer inspection system corresponding to different locations in a die where the POI exists. In this manner, one can construct an "average" image or a "median" image by taking the pixel-wise average (or median) over a collection of image patches corresponding to different locations in the die where a given POI exists. For example, the golden patch image may be constructed as a median of 8 die images. In one embodiment, generating the standard reference patch image from the multiple image patches includes aligning the multiple image patches to each other with sub-pixel accuracy and processing the aligned multiple image patches together. For example, when computing an average or median patch image, it is necessary to align to sub-pixel accuracy the patches that are being averaged (or whose median value is being computed). The standard reference patch (golden patch) for each POI type (group) is stored in the inspection recipe for use during inspection. For example, in one embodiment, the steps of scanning the wafer and detecting the defects described further herein are performed with a wafer inspection recipe, and the method includes storing a standard reference patch image for the POI and any other POIs different than the POI in the wafer inspection recipe.

In one embodiment, detecting the defects includes aligning a standard reference patch image for the POI to the output generated by the wafer inspection system to determine the output corresponding to the POI and applying one or more defect detection algorithms to only a portion of the output corresponding to the POI, and the portion of the output corresponds to only the weak geometry in the POI. For example, during inspection, as each swath is processed, the corresponding POI locations in the die would be accessed (call this the test patch), and the particular standard reference patch (stored in the recipe) for that location would be aligned to the test patch. After alignment and sub-pixel interpolation, a comparison of the two patches would be performed. Any of several methods can be employed for performing this image comparison in order to flag potential defective pixels in the test image. Note that only the pixels within the MCA are examined for potential defects. The larger POI is used only for alignment purposes and potentially for measuring the noise level in order to set the detection threshold. This threshold is applied to the gray level difference image obtained by subtracting the test patch pixel value from the standard reference patch pixel value at each location in the POI. In addition, during an inspection run, the golden patch may be compared with every test die image, and detection may be performed in any suitable way using a single detection algorithm or any other detection algorithm. In other words, once the images are compared with the golden patch, defect detection may proceed as usual with any currently used defect detection algorithm(s) or method(s). In this manner, the embodiments described herein are not limited to the types of defect detection that can be used.

Figure 3:
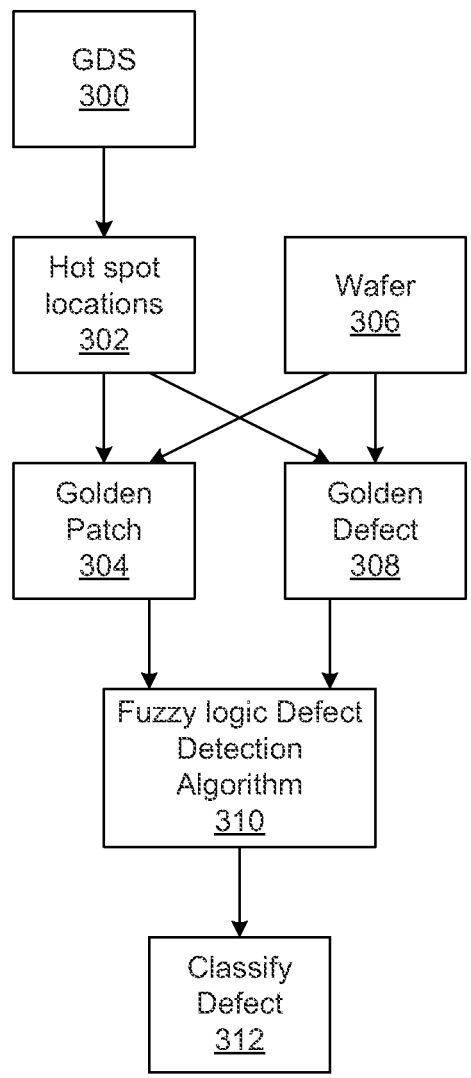
FIGS. 3 and 4 are flow charts illustrating embodiments of a method for detecting defects on a wafer.

FIG. 3 shows various embodiments of a processing flow during inspection. In particular, as shown in FIG. 3, GDS 300 may be used to determine hot spot locations 302, which may be performed as described further herein. Wafer 306 may then be scanned using a wafer inspection system as described herein. Patch images in the output generated by the wafer inspection system may then be compared to golden patch 304, which can be acquired or generated according to any of the embodiments described herein. Fuzzy logic defect detection algorithm 310 may then be applied to the results of the patch to golden patch comparison. Based on the output of the fuzzy logic defect detection algorithm, the defects can be classified as shown in step 312.

The patch to golden patch and golden defect method is identical to the method described above (patch to golden patch) except that in this case an example of a defect image in the hot spot area is also provided. For example, in one embodiment, the method includes generating a standard reference patch image for the POI and a standard defect image for the weak geometry in the POI. The image is assumed to be from a wafer of the same device/layer and scanned on the same type of inspection tool and with the same imaging conditions as used for inspection of subsequent wafers of that device at that layer. For example, in one embodiment, the standard defect image is acquired by scanning an additional wafer of the same design and layer as the wafer with the wafer inspection system and the same imaging conditions used for scanning the wafer. A priori knowledge about how the defect looks or where it is located can be used to find defects and clean (non-defect) locations without using some form of image comparison.

FIG. 3 shows an embodiment of the processing flow during this inspection. This method may include all of the steps of FIG. 3 described above. Note that, in this case, each test patch is compared with not only the corresponding golden patch but also the example of the defect (called a golden defect). In other words, in one embodiment, detecting the defects includes comparing the output generated for one instance of the weak geometry with the standard reference patch image and comparing the output generated for the one instance of the weak geometry with the standard defect image. For example, as shown in FIG. 3, the method in this embodiment includes comparing output generated for wafer 306 by the wafer inspection system with both golden patch 304 and golden defect 308, which may be acquired or generated according to any of the embodiments described herein. In this embodiment of the method, fuzzy logic defect detection algorithm 310 may be applied to the results of both the comparison of the output to the golden patch and the comparison of the output to the golden defect. The test image can be compared with both the golden patch and the golden defect images and a measure of similarity can be computed.

The use of a defect image provides additional information that can be used to prevent nuisance detections (false positives) by ensuring that the test patch bears a similarity with the golden defect and is sufficiently different from the golden patch (defect-free image). In this manner, in one embodiment, detecting the defects includes determining that a potential defect is located in the one instance of the weak geometry if the output generated for the one instance of the weak geometry and the standard reference patch image are different and if the output generated for the one instance of the weak geometry and the standard defect image are substantially the same. A number of statistical classification techniques can be used to implement this logic shown in FIG. 3 as "fuzzy logic defect detection algorithm."

The interpolation distance between the golden patch and golden die and the test image may be relatively high and as a result the interpolation noise could be a limit to the achievable sensitivity. However, the interpolation noise will always be lower than the die-to-die noise. In addition, the embodiments described herein may have somewhat higher computation costs than currently used inspection methods, but those computation costs can be mitigated because the number of pixels being inspected can be reduced (e.g., to just hot spots) compared to currently used inspection methods.

In the previously described methods, each test patch is compared with a golden patch or a golden patch and golden defect and a decision is made on whether a defect exists in the test patch or not. In the aggregate patch outlier detection method, the decision on whether a test patch is defective or not is only made by examining the aggregated properties of all test patches (belonging to a certain POI group). For example, in one embodiment, detecting the defects includes determining aggregated properties for the output generated at all instances of the weak geometry and determining if the at least one instance of the weak geometry includes a defect based on the aggregated properties. This aggregation can be done at the sub-die level (e.g., the die could be split into N regions), or at the whole die level. For example, in one embodiment, detecting the defects includes determining aggregated properties for the output generated in instances of the weak geometry in only a portion of a die and determining if the at least one instance of the weak geometry includes a defect based on the aggregated properties.

The advantage of this method is that the decision on what constitutes a defect is made in an "adaptive" manner, i.e., an outlier is defined in terms of the population of the aggregate set of patches. Thus, this method is less prone to flagging nuisance events that can arise due to wafer-to-wafer variations such as would be the case for the single golden patch methods described earlier. In particular, since the golden patch may be derived from a given wafer, the imaging conditions could be slightly different on the test wafer and this could result in false positives. The aggregate method avoids such false positives because each pixel in the MCA is compared with respect to the distribution of the corresponding pixels in each of the other test patches in the sub-dies or dies. This comparison automatically makes the golden die pixel values irrelevant since one could just as well look at the outliers on the tails of the individual pixel gray level histograms. Note that the golden patch is still used to locate the instances of the geometry in the die. Note also that when computing the individual pixel histograms, the geometries have to be aligned to sub-pixel accuracy. Thus, each test patch should be interpolated to align to a common pixel grid. Variations in background color can be removed by applying a color filter to the test patches and equalizing their average background before computing the pixel histograms.

Figure 4:
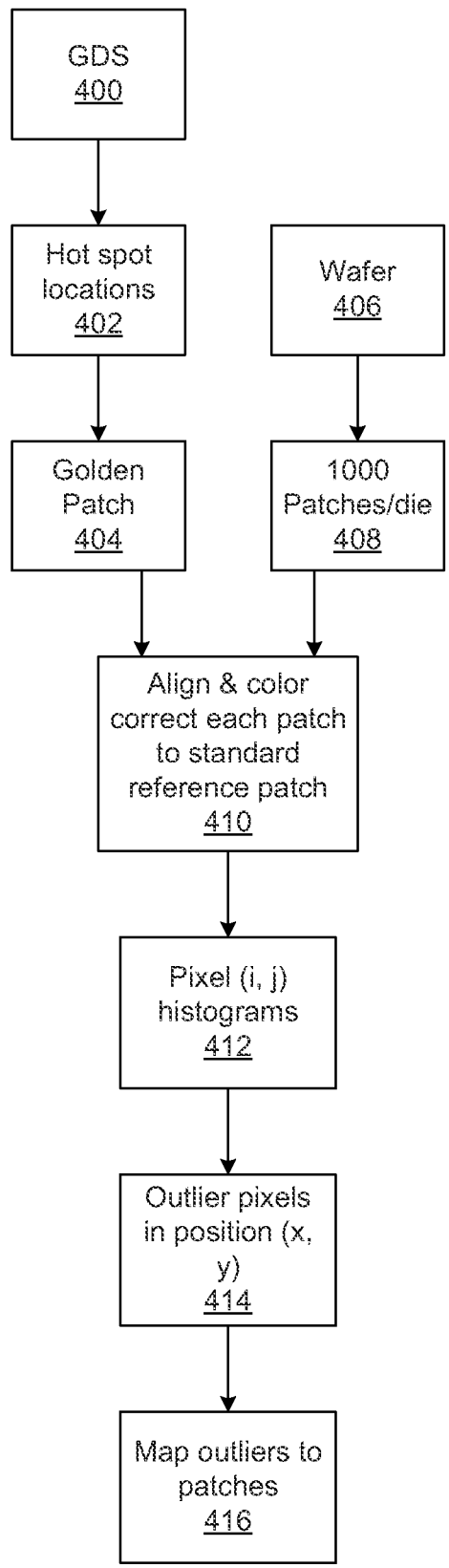

FIG. 4 shows one embodiment of such a method. For example, as shown in FIG. 4, GDS 400 may be used to determine hot spot locations 402 as described further herein. Based on the hot spot locations, golden patch 404 can be acquired or generated according to any of the embodiments described herein. Wafer 406 can be scanned by an inspection system as described herein and output can be acquired for a number of patches per die such as 1000 patches/die as shown in step 408 of FIG. 4. For example, 1000 (or some other number) of hot spot locations can be grabbed from a given die. As shown in step 410 of FIG. 4, the method may include aligning and color correcting each patch to a standard reference patch. Pixel (i, j) histograms 412 may then be generated. For example, for each pixel in the hot spot area, a difference histogram with respect to the corresponding pixel from the standard reference patch may be computed (e.g., in an area of 5 pixels by 5 pixels). The method may then include identifying outlier pixels in position (x, y) 414 based on the pixel histograms. For example, outliers may be found using each pixel's histogram. In the example described above, there would be 25 histograms. In this manner, 1000 hot spots (e.g., where each hot spot includes, say, 5×5 pixels) can be examined for potential outliers. The method may further include mapping outliers to patches as shown in step 416 of FIG. 4. In this manner, each of the patches that corresponds to an outlier can be identified. The method may also include selecting as (soft) repeaters those patches where the outliers from the above step "cluster" spatially.

Each of the embodiments of the methods described above may include any other step(s) of any other method(s) described herein. Furthermore, each of the embodiments of the methods described above may be performed by any of the systems described herein.

All of the methods described herein may include storing results of one or more steps of the method embodiments in a computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc.

Figures 5, 6:
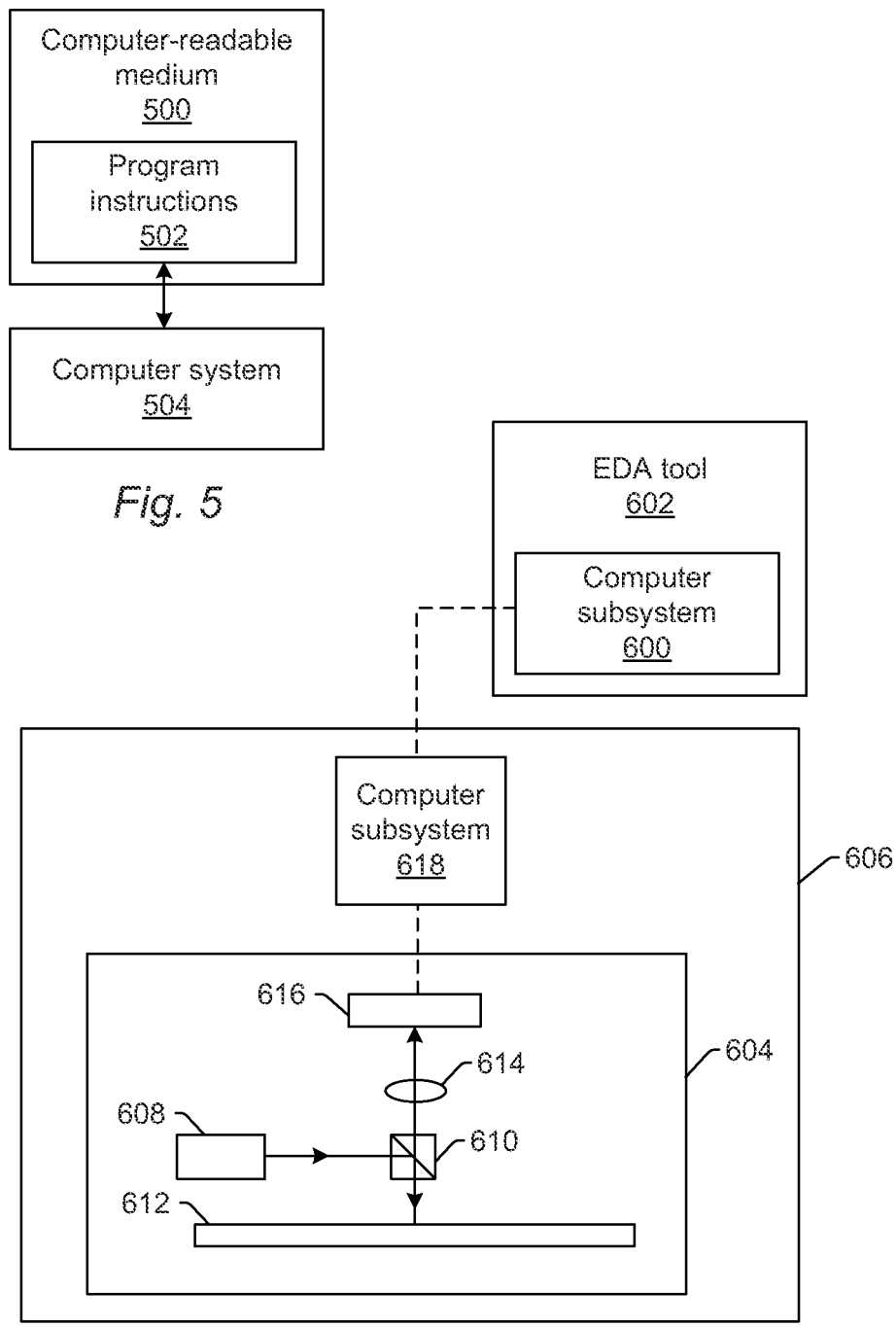
FIG. 5 is a block diagram illustrating one embodiment of a non-transitory computer-readable medium storing program instructions for causing a computer system to perform a computer-implemented method described herein.
FIG. 6 is a schematic diagram illustrating a side view of an embodiment of a system configured to detect defects on a wafer.

Another embodiment relates to a non-transitory computer-readable medium storing program instructions executable on a computer system for performing a computer-implemented method for detecting defects on a wafer. One such embodiment is shown in FIG. 5. For example, as shown in FIG. 5, non-transitory computer-readable medium 500 stores program instructions 502 executable on computer system 504 for performing a computer-implemented method for detecting defects on a wafer. The computer-implemented method may include any step(s) of any method(s) described herein.

Program instructions 502 implementing methods such as those described herein may be stored on non-transitory computer-readable medium 500. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

Computer system 504 may take various forms, including a personal computer system, mainframe computer system, workstation, system computer, image computer, programmable image computer, parallel processor, or any other device known in the art. In general, the term "computer system" may be broadly defined to encompass any device having one or more processors, which executes instructions from a memory medium.

An additional embodiment relates to a system configured to detect defects on a wafer. The system includes one or more computer subsystems configured for determining locations of all instances of a weak geometry in a design for a wafer. The locations include random, aperiodic locations, and the weak geometry includes one or more features that are more prone to defects than other features in the design. The computer subsystem(s) may be configured to perform this step as described further herein.

In one embodiment, the computer subsystem(s) described above are part of an electronic design automation (EDA) tool, and the inspection subsystem described further herein is not part of the EDA tool. For example, as shown in FIG. 6, the computer subsystem(s) described above may include computer subsystem 600 included in EDA tool 602. The EDA tool and the computer subsystem(s) included in such a tool may include any commercially available EDA tool that can be configured to perform the steps described above. Therefore, the computer subsystem(s) that determine the locations of all instances of the weak geometry may be separate from an inspection subsystem of an inspection tool that is used to inspect the wafer. In other words, the design may be processed by one system or tool to determine the locations of the weak geometry instances that will be used by another, different system or tool to detect defects.

The computer subsystem(s) that are used to determine the locations of the weak geometry instances also may not be part of an EDA tool and may be included in another system or tool or simply be configured as a stand alone computer system. Furthermore, the tool or computer subsystem that determines the weak geometry locations may be configured to provide that information to the other tool by storing or transferring information for the weak geometry locations to a shared computer-readable storage medium such as a fab database or by transmitting information for the weak geometry locations directly to the tool that will use it, which may be performed as described further herein.

The system also includes an inspection subsystem configured to scan a wafer to thereby generate output for the wafer with one or more detectors of the inspection subsystem. One embodiment of such an inspection subsystem is shown in FIG. 6 as inspection subsystem 604 of system 606. The inspection subsystem is configured to scan the wafer by scanning the wafer with light and detecting light from the wafer during the scanning. For example, as shown in FIG. 6, the inspection subsystem includes light source 608, which may include any suitable light source known in the art.

Light from the light source may be directed to beam splitter 610, which may be configured to direct the light from the light source to wafer 612. The light source may be coupled to any other suitable elements (not shown) such as one or more condensing lenses, collimating lenses, relay lenses, objective lenses, apertures, spectral filters, polarizing components and the like. As shown in FIG. 6, the light may be directed to the wafer at a normal angle of incidence. However, the light may be directed to the wafer at any suitable angle of incidence including near normal and oblique incidence. In addition, the light or multiple light beams may be directed to the wafer at more than one angle of incidence sequentially or simultaneously. The inspection subsystem may be configured to scan the light over the wafer in any suitable manner.

Light from wafer 612 may be collected and detected by one or more detectors of the inspection subsystem during scanning. For example, light reflected from wafer 612 at angles relatively close to normal (i.e., specularly reflected light when the incidence is normal) may pass through beam splitter 610 to lens 614. Lens 614 may include a refractive optical element as shown in FIG. 6. In addition, lens 614 may include one or more refractive optical elements and/or one or more reflective optical elements. Light collected by lens 614 may be focused to detector 616. Detector 616 may include any suitable detector known in the art such as a charge coupled device (CCD) or another type of imaging detector. Detector 616 is configured to generate output that is responsive to the reflected light collected by lens 614. Therefore, lens 614 and detector 616 form one channel of the inspection subsystem. This channel of the inspection subsystem may include any other suitable optical components (not shown) known in the art. The output of the detector may include, for example, images, image data, signals, image signals, or any other output that can be generated by a detector suitable for use in an inspection system.

Since the inspection subsystem shown in FIG. 6 is configured to detect light specularly reflected from the wafer, the inspection subsystem is configured as a bright field (BF) inspection system. Such an inspection subsystem may, however, also be configured for other types of wafer inspection. For example, the inspection subsystem shown in FIG. 6 may also include one or more other channels (not shown). The other channel(s) may include any of the optical components described herein such as a lens and a detector, configured as a scattered light channel. The lens and the detector may be further configured as described herein. In this manner, the inspection subsystem may also be configured for dark field (DF) inspection.

The computer subsystem(s) of the system may use output generated by detector 616 and/or any other detectors included in the inspection subsystem to detect defects on the wafer as described herein. For example, the system may also include computer subsystem 618 that is coupled to the inspection subsystem. In this manner, output generated by the detector(s) of the inspection subsystem may be provided to computer subsystem 618. Computer subsystem 618 is configured to detect defects in at least one instance of the weak geometry based on the output generated at two or more instances of the weak geometry in a single die on the wafer. Computer subsystem 618 may be configured to perform any other steps described herein.

Computer subsystem 618 may also be coupled to the other computer subsystem that is not part of the inspection system such as computer subsystem 600, which may be included in another tool such as the EDA tool described above such that computer subsystem 618 can receive output generated by computer subsystem 600, which may include the information for the weak geometry locations for the wafer being inspected. For example, the two computer subsystems may be effectively coupled by a shared computer-readable storage medium such as a fab database or may be coupled by a transmission medium such as that described above such that information may be transmitted between the two computer subsystems.

It is noted that FIG. 6 is provided herein to generally illustrate a configuration of an inspection subsystem that may be included in the system embodiments described herein. Obviously, the inspection subsystem configuration described herein may be altered to optimize the performance of the inspection subsystem as is normally performed when designing a commercial inspection system. In addition, the systems described herein may be implemented using an existing inspection subsystem (e.g., by adding functionality described herein to an existing inspection system) such as the 29xx/28xx series of tools that are commercially available from KLA-Tencor, Milpitas, Calif. For some such systems, the methods described herein may be provided as optional functionality of the system (e.g., in addition to other functionality of the system). Alternatively, the system described herein may be designed "from scratch" to provide a completely new system. In addition, the embodiments described herein can be implemented by modifying existing, commercially available software to perform one or more embodiments of the methods described herein. For example, the embodiments described herein may be implemented with or combined with the NanoPoint product that is commercially available from KLA-Tencor to provide NanoPoint repeater detection.

Furthermore, although the system is described herein as being an optical or light-based inspection system, the inspection subsystem may be configured as an electron beam based inspection subsystem. The electron beam based inspection subsystem may be any suitable electron beam based inspection subsystem included in any suitable commercially available electron beam inspection system.

Further modifications and alternative embodiments of various aspects of the invention will be apparent to those skilled in the art in view of this description. For example, systems and methods for detecting defects on a wafer are provided. Accordingly, this description is to be construed as illustrative only and for the purpose of teaching those skilled in the art the general manner of carrying out the invention, it is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for detecting defects on a wafer, comprising: determining locations of all instances of a weak geometry in a design for a wafer, wherein the locations comprise random, aperiodic locations, and wherein the weak geometry comprises one or more features that are more prone to defects than other features in the design; scanning the wafer with a wafer inspection system to thereby generate output for the wafer with one or more detectors of the wafer inspection system; and detecting defects in one instance of the weak geometry based on the output generated at two or more instances of the weak geometry at the random, aperiodic locations in a single die on the wafer, wherein said determining and said detecting are performed with one or more computer systems.

2. The method of claim 1, wherein the weak geometry is specified in a window at a point in design coordinate space, and wherein a width and a height of the window are less than or equal to 100 nm.

3. The method of claim 2, wherein instances of the window in the design constitute at least some micro care areas for inspection of the wafer.

4. The method of claim 2, further comprising creating a larger window around the window, wherein features in the larger window are used as a pattern of interest for inspection of the wafer.

5. The method of claim 4, wherein detecting the defects comprises aligning the features in the larger window to patch images in the output.

6. The method of claim 4, further comprising determining design context for weak geometry based on the features in the larger window.

7. The method of claim 4, further comprising grouping all instances of the pattern of interest that are substantially the same into one bin and all other instances of patterns of interest into one or more other bins.

8. The method of claim 4, further comprising generating a standard reference patch image for the pattern of interest by acquiring an image of at least one instance of the pattern of interest with the wafer inspection system.

9. The method of claim 4, further comprising generating a standard reference patch image for the pattern of interest from multiple image patches acquired b e wafer inspection system corresponding to different locations in a die where the pattern of interest exists.

10. The method of claim 9, wherein generating the standard reference patch image from the multiple image patches comprises aligning the multiple image patches to each other with sub-pixel accuracy and processing the aligned multiple image patches together.

11. The method of claim 4, wherein scanning the wafer and detecting the defects are performed with a wafer inspection recipe, and wherein the method further comprises storing a standard reference patch image for the pattern of interest and any other patterns of interest different than the pattern of interest in the wafer inspection recipe.

12. The method of claim 4, wherein detecting the defects comprises aligning a standard reference patch image for the pattern of interest to the output generated by the wafer inspection system to determine the output corresponding to the pattern of interest and applying one or more defect detection algorithms to only a portion of the output corresponding to the pattern of interest, and wherein the portion of the output corresponds to only the weak geometry in the pattern of interest.

13. The method of claim 4, further comprising generating a standard reference patch image for the pattern of interest and a standard defect image for the weak geometry in the pattern of interest.

14. The method of claim 13, wherein the standard defect image is acquired by scanning an additional wafer of the same design and layer as the wafer with the wafer inspection system and the same imaging conditions used for scanning the wafer.

15. The method of claim 13, wherein detecting the defects comprises comparing the output generated for the one instance of the weak geometry with the standard reference patch image and comparing the output generated for the one instance of the weak geometry with the standard defect image.

16. The method of claim 15, wherein detecting the defects further comprises determining that a potential defect is located in the one instance of the weak geometry if the output generated for the one instance of the weak geometry and the standard reference patch image are different and if the output generated for the one instance of the weak geometry and the standard defect image are substantially the same.

17. The method of claim 1, wherein detecting the defects comprises determining aggregated properties for the output generated at said all instances of the weak geometry and determining if the one instance of the weak geometry includes a defect based on the aggregated properties.

18. The method of claim 1, wherein detecting the defects comprises determining aggregated properties for the output generated in instances of the weak geometry in only a portion of a die and determining if the one instance of the weak geometry includes a defect based on the aggregated properties.

19. A non-transitory computer-readable medium, storing program instructions executable on a computer system for performing a computer-implemented method for detecting defects on a wafer, wherein the computer-implemented method comprises:
determining locations of all instances of a weak geometry in a design for a wafer, wherein the locations comprise random, aperiodic locations, and wherein the weak geometry comprises one or more features that are more prone to defects than other features in the design;
scanning the wafer with a wafer inspection system to thereby generate output for the wafer with one or more detectors of the wafer inspection system; and
detecting defects in one instance of the weak geometry based on the output generated at two or more instances of the weak geometry at the random, aperiodic locations in a single die on the wafer.

20. A system configured to detect defects on a wafer, comprising:
an inspection subsystem configured to scan a wafer to thereby generate output for the wafer with one or more detectors of the inspection subsystem; and
one or more computer subsystems configured for:
determining locations of all instances of a weak geometry in a design for the wafer, wherein the locations comprise random, aperiodic locations, and wherein the weak geometry comprises one or more features that are more prone to defects than other features in the design; and
detecting defects in one instance of the weak geometry based on the output generated at two or more instances of the weak geometry at the random, aperiodic locations in a single die on the wafer.

21. The system of claim 20, wherein the weak geometry is specified in a window at a point in design coordinate space, and wherein a width and a height of the window are less than or equal to 100 nm.

22. The system of claim 21, wherein instances of the window in the design constitute at least some micro care areas for inspection of the wafer.

23. The system of claim 21, wherein the one or more computer subsystems are further configured for creating a larger window around the window, and wherein features in the larger window are used as a pattern of interest for inspection of the wafer.

24. The system of claim 23, wherein detecting the defects comprises aligning the features in the larger window to patch images in the output.

25. The system of claim 23, wherein the one or more computer subsystems are further configured for determining design context for the weak geometry based on the features in the larger window.

26. The system of claim 23, wherein the one or more computer subsystems are further configured for grouping all instances of the pattern of interest that are substantially the same into one bin and all other instances of patterns of interest into one or more other bins.

27. The system of claim 23, wherein the one or more computer subsystems are further configured for generating a standard reference patch image for the pattern of interest by acquiring an image of at least one instance of the pattern of interest with the inspection subsystem.

28. The system of claim 23, wherein the one or more computer subsystems are further configured for generating a standard reference patch image for the pattern of interest from multiple image patches acquired by the inspection subsystem corresponding to different locations in a die where the pattern of interest exists.

29. The system of claim 28, wherein generating the standard reference patch image from the multiple image patches comprises aligning the multiple image patches to each other with sub-pixel accuracy and processing the aligned multiple image patches together.

30. The system of claim 23, wherein the inspection subsystem is further configured to scan the wafer using a wafer inspection recipe, wherein detecting the defects is performed with the wafer inspection recipe, and wherein the one or more computer subsystems are further configured for storing a standard reference patch image for the pattern of interest and any other patterns of interest different than the pattern of interest in the wafer inspection recipe.

31. The system of claim 23, wherein detecting the defects comprises aligning a standard reference patch image for the pattern of interest to the output generated by the inspection subsystem to determine the output corresponding to the pattern of interest and applying one or more defect detection algorithms to only a portion of the output corresponding to the pattern of interest, and wherein the portion of the output corresponds to only the weak geometry in the pattern of interest.

32. The system of claim 23, wherein the one or more computer subsystems are further configured for generating a standard reference patch image for the pattern of interest and a standard defect image for the weak geometry in the pattern of interest.

33. The system of claim 32, wherein the standard defect image is acquired by scanning an additional wafer of the same design and layer as the wafer with the inspection subsystem and the same imaging conditions used for scanning the wafer.

34. The system of claim 32, wherein detecting the defects comprises comparing the output generated for the one instance of the weak geometry with the standard reference patch image and comparing the output generated for the one instance of the weak geometry with the standard defect image.

35. The system of claim 34, wherein detecting the defects further comprises determining that a potential defect is located in the one instance of the weak geometry if the output generated for the one instance of the weak geometry and the standard reference patch image are different and if the output generated for the one instance of the weak geometry and the standard defect image are substantially the same.

36. The system of claim 20, wherein detecting the defects comprises determining aggregated properties for the output generated at said all instances of the weak geometry and determining if the one instance of the weak geometry includes a defect based on the aggregated properties.

37. The system of claim 20, wherein detecting the defects comprises determining aggregated properties for the output generated in instances of the weak geometry in only a portion of a die and determining if the one instance of the weak geometry includes a defect based on the aggregated properties.

\* \* \* \* \*